United States Patent [19]

Chang

[11] 4,101,957

[45] Jul. 18, 1978

[54] ZOOM OPERATING LIGHT

[76] Inventor: Bansun Chang, 12010 Susan Dr., Granada Hills, Calif. 91344

[21] Appl. No.: 722,220

[22] Filed: Sep. 10, 1976

[51] Int. Cl.$^2$ .............................................. A61B 1/06
[52] U.S. Cl. .................................... 362/268; 362/293; 362/296
[58] Field of Search .............. 240/41.15, 41.3, 41 R, 240/1.4; 128/23; 350/184; 362/268, 277, 293, 296

[56] References Cited

U.S. PATENT DOCUMENTS

| 1,695,556 | 12/1928 | McGunnigle | 240/41.15 UX |
| 3,469,145 | 9/1969 | Ralke et al. | 240/11.4 R X |
| 3,711,700 | 1/1973 | Westlund et al. | 240/41.15 |
| 3,930,149 | 12/1975 | French | 240/41.15 |

FOREIGN PATENT DOCUMENTS

| 1,023,894 | 3/1966 | United Kingdom | 240/41.15 |

*Primary Examiner*—John Gonzales
*Attorney, Agent, or Firm*—Francis X. LoJacono

[57] ABSTRACT

An illuminating lamp for use in dentistry or medical clinic which provides for varying both the intensity of light output and the size of the illuminated area while maintaining a substantially constant color temperature. In this illuminating lamp, a light source consisting of a high intensity halogen bulb positioned horizontally at the inner focus of an ellipsoidal reflector projects through the aperture of a radiation reflecting disc; the light beam then converges at the external conjugating focus before reaching an optical zoom unit consisting of a heat absorbing filter positioned between one fixed and one movable lens. The beam intensity and its projected illumination area are manipulated with the zoom mechanism while the light beam spectral color temperature is controlled by the characteristics of a heat absorbing filter in conjunction with a spectral correction coating on the backside of the front covering glass. In addition, a special electrical circuit has been provided to eliminate the "cold-shock" to the filament of the halogen bulb in order to prolong its service life, along with an surge interruptor for the on-off switch in order to eliminate the possibility of a fire hazard throughout the electrical power system.

4 Claims, 10 Drawing Figures

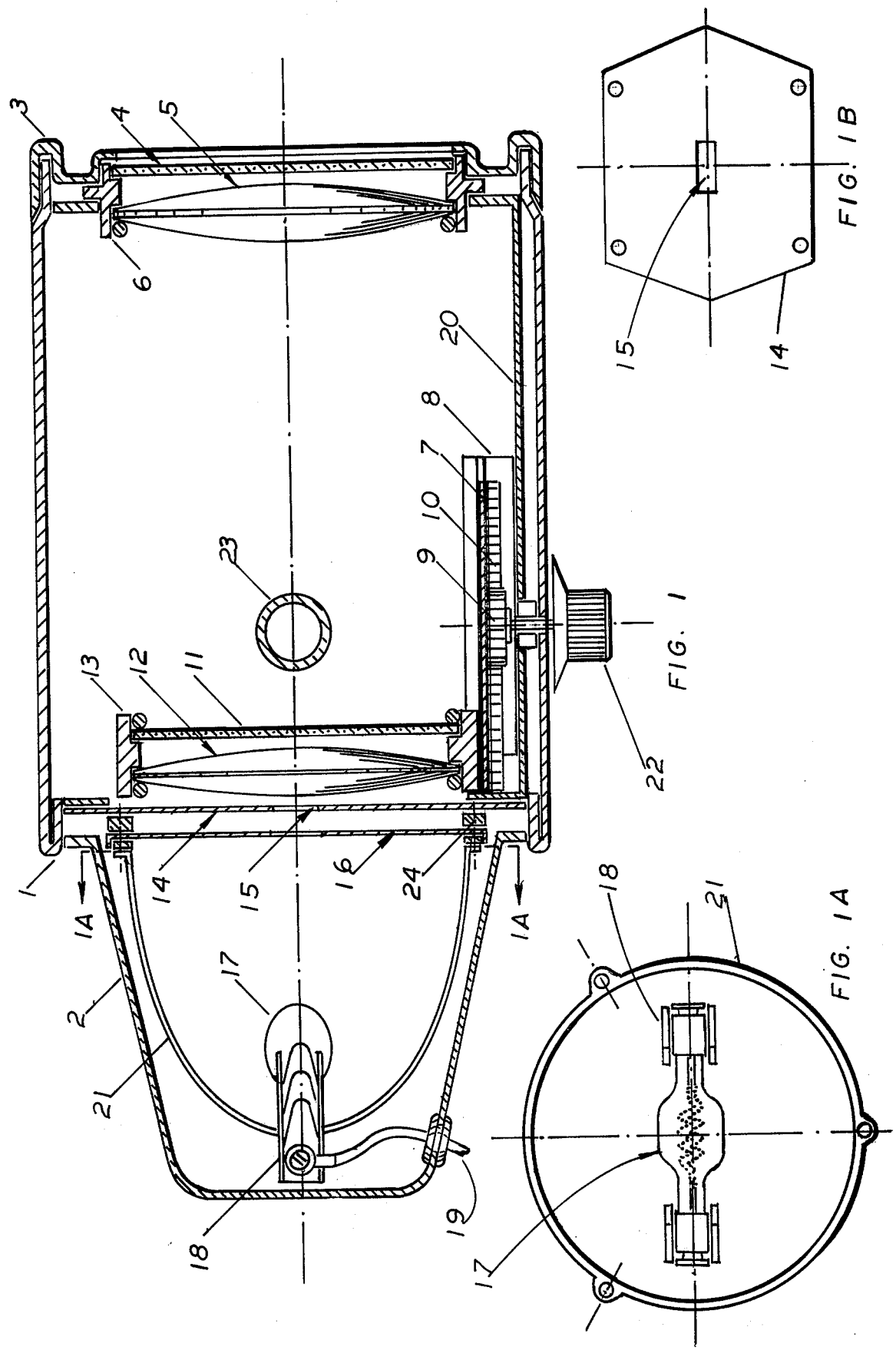

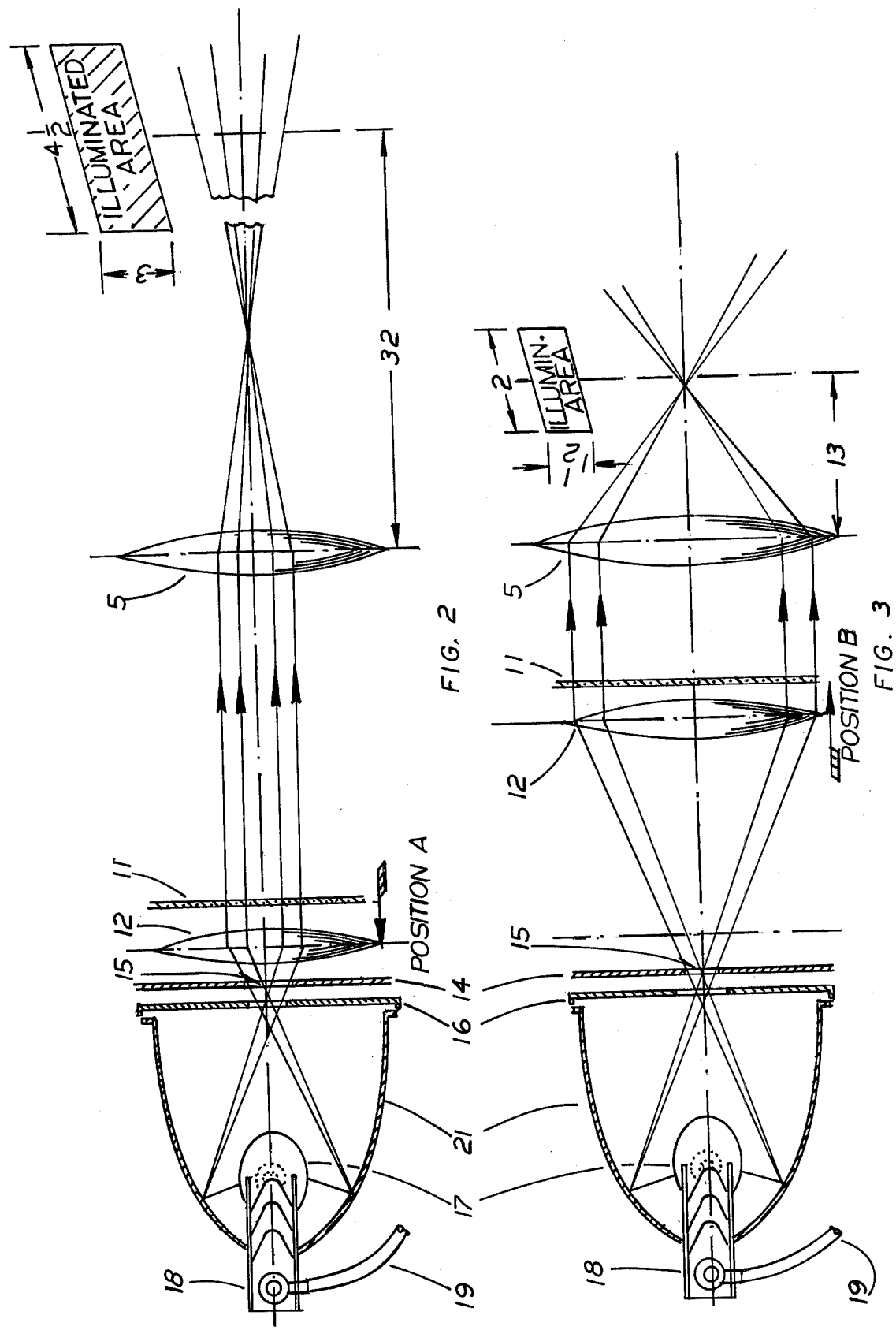

SPECTRAL TRANSMISSION CHARACTERISTICS OF KG 1 OPTICAL GLASS FROM VISIBLE REGION THROUGH THE FAR INFRA RED REGION

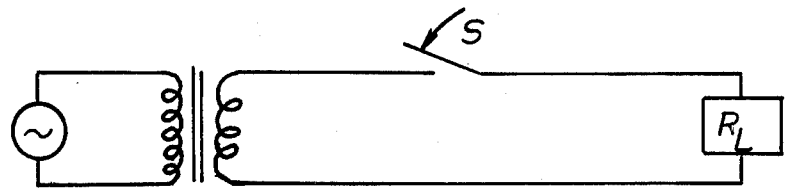
FIG. 5a  A SIMPLIFIED ELECTRICAL CIRCUIT
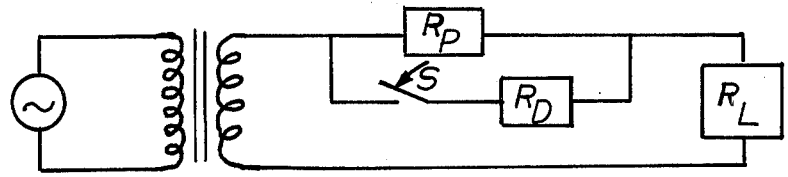
FIG. 5b  THE MODIFIED ELECTRICAL CIRCUIT
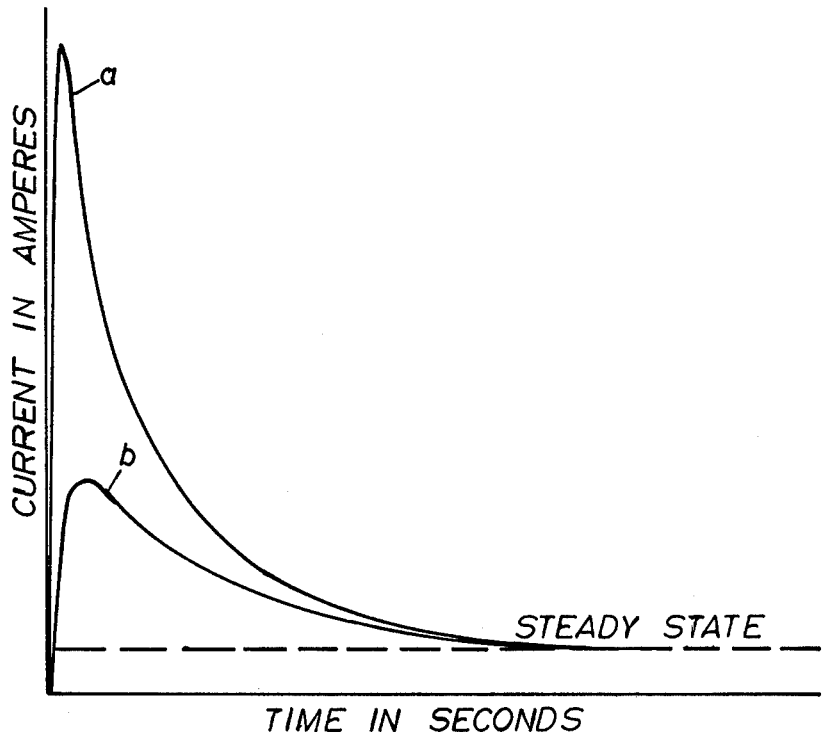
FIG. 5c  THE TYPICAL CURRENT TRANSIENT DIAGRAM
OF A RESISTIVE LOAD CIRCUIT

ZOOM OPERATING LIGHT

BACKGROUND OF THE INVENTION

1. Field of Invention

This invention relates to lighting appliances for dental and medical clinics and in particular to such devices which utilize the combination of an optical zoom mechanism, a heat absorbing filter, and a controllable iris to provide a truly cold variable intensity, sharp focused light beam onto the projected objective area.

2. Brief Summary of Prior Art

The dental operating lights can be generally divided into two groups: (1) those using a light source at one focus of a dichroic-film coated ellipsoidal glass reflector whereupon the reflected light beam is loosely and openly converged at the other focal point, forming an irregular-shaped illuminated area; and (2) those using a light source at one focus of an ellipsoidal metallic reflector that projects at the other focus on an aperture having an opening defining the extent of the beam, and using a heat absorbing filter to eliminate the infrared energy from the lamp. The former group provides a high intensity light on the patient's face in an uncontrollable irregular pattern with most of the infrared portion of the radiation energy produced by the light source resulting in undesirable heating the face of the patient as well as the arms, shoulder, and head of the dentist or doctor. In addition, the color temperature of the illuminating light will change continuously due to the oxidation of the dichroic coating produced by the high intensity heat energy of the light source and the moisture from the air. The latter group generally use a vertically oriented cylindrical bulb mounted in either a bayonet or threaded socket protruding from the end of the ellipsoidal reflector to the nearest conjugate focus. Since the radiation pattern of the vertically oriented cylindrical bulb is inherently circular, conversion of the circular pattern to the desired horizontally oriented pattern will either induce some deficiency in the horizontal dimension of the illuminated area, or sacrifice radiation energy in the vertical direction. In addition, the socket and the base of the light bulb will quite often fuse together after a certain length of service. Consequently, lamp burnout requires costly system replacement instead of the simple replacement of the light bulb. Furthermore, in those lamps that utilize a moving light source relative to a fixed aperture, there is no real advantage to varying the beam intensity since most of its illuminated pattern will be fuzzy and dim except at one single position where the converged light beams are focused right at the light gate.

Moreover, most of these operating lights are subject to the problem of A. C. switching surge (or arcing) which can produce a fire hazard throughout the electrical supply circuit when its on-off switch is used for a certain length of time. In addition, each time the lamp is turned on or off, a "cold-shock" effect acts on the filament of the light bulb, severely limiting the actual service life of the light bulb.

BRIEF SUMMARY OF INVENTION

This invention solves these problems by using (1) an optical zoom assembly consisting of one fixed and one moving biconvex lens in line with a special heat absorbing filter, to provide for varying both the light intensity as well as the size of the projected illuminated area; (2) an appropriately positioned specific heat absorbing filter to provide a truly cold beam of light in conjunction with a dual-function spectral correction front covering glass located far from the high intensity light source in order to produce a balanced constant color temperature light beam; (3) a special A. C. surge interruptor circuit introduced into the electrical supply line in order to suppress switching arc, eliminating any possible fire hazard; and (4) a low energy pre-heating circuit in order to eliminate the "cold-shock" effect on the light source filament.

The illuminating optical system of the invention uses a horizontally oriented high intensity incandescent bulb, an ellipsoidal reflector, a radiation reflecting disc, and a focal plane pattern forming iris plate in order to project a horizontal radiation beam onto a zoom unit consisting of two biconvex lens with a special heat absorbing filter stationed between them. Since the filament of the horizontally oriented bulb is located in the near end focal point of the ellipsoidal reflector, and the emanating beam is re-shaped at the other conjugate focal point of the ellipsoidal reflector with the aid of a radiation reflecting disc, the amount of radiant light energy emanating from the light source will be maximized into a radiant bundle before reaching the optical zoom unit. The light beam output may be manipulated into any rectangular illumination pattern at any appropriate distance as one desires. The true cold and color-balanced light beam is produced by positioning a heat absorbing filter about one half inch behind the first biconvex lens of the moving platform of the zoom unit in order to remove the radiant infrared energy from the projected light source.

OBJECTIVES AND ADVANTAGES OF THE INVENTION

The primary objective of this invention is to provide the dental and medical communities with an illuminating operating light which incorporates several advances in functional design for both improved characteristics of illumination and user safety during operation.

The basic advantages of this invention can be summarized as follows:

(1) A sharply focused variable-intensity and variable size truly cold light beam will be projected to the desired spot with the control of an optical zoom mechanism.

(2) The balance of spectral color temperature in the visible region can be easily achieved with the combination of the spectral heat absorbing filter and the dual function spectral correction front covering glass. Moreover, most heat absorbing filter are prone to weathering effects. A special housing is provided to avoid this environmental hazard.

(3) The light source is horizontally oriented, and its filament is placed horizontally at the conjugate focus of the ellipsoidal reflector in order to generate a horizontally oriented emitting beam for high operational efficiency. The high intensity halogen bulb is mounted on a pair of leaf-spring loaded porcelain sockets, which will eliminate any possibility of bulb-socket fusing.

(4) A combination of filament ballast and a resistive switch-arc interruptor circuit is provided to eliminate the "cold-shock" effect on the filament and the potential fire hazard of the electrical power supply system.

BRIEF DESCIPTION OF THE DRAWING

Other features, objects and advantages of the invention will be apparent from the following specifications, taken in conjunction with the accompanying drawings in which:

FIG. 1 is a side elevation view of the dental operating lamp of the invention with the side housing cover removed;

FIG. 1A is the cross-sectional view of the light source revolved 90° from FIG. 1 around the minor axis of the ellipsoidal reflector;

FIG. 1B is a simplified scaled-down plain view of the focal plane iris plate;

FIG. 2 is an illustration of the major components in the zoom operating light positioned for longer distance illumination;

FIG. 3 is an illustration of the major components in the zoom operating light positioned for short distance and high intensity illumination;

FIGS. 5a and 5b illustrate the major components of the two load circuit;

Figure 4A:
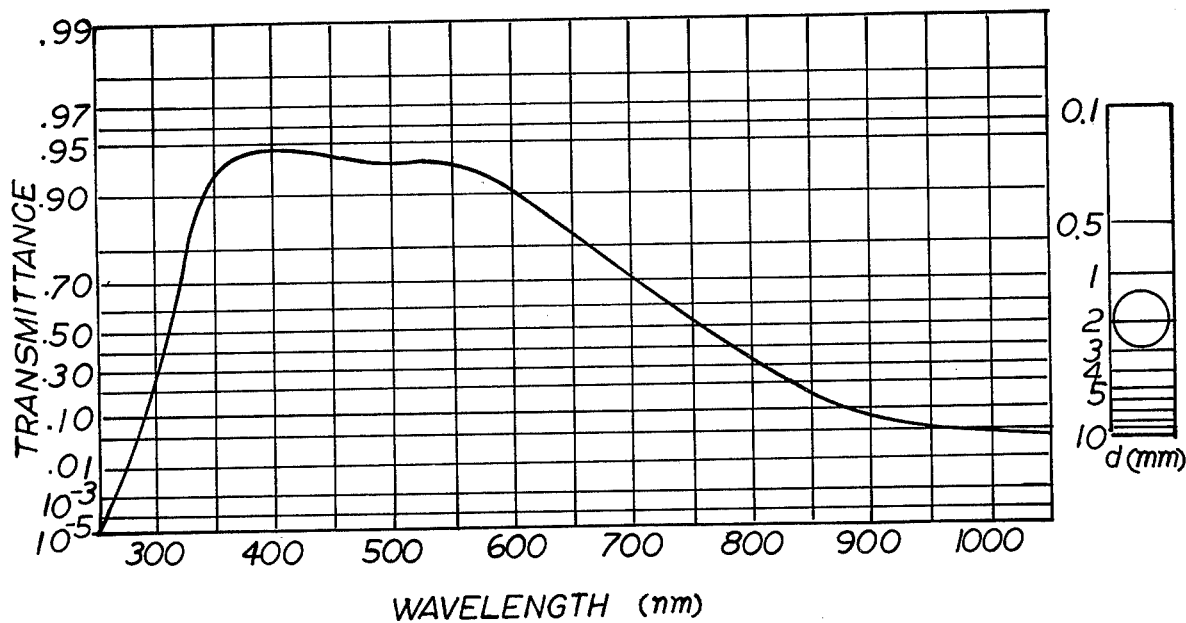
FIGS. 4 and 4a illustrate spectral transmission characteristics of the KG-1 heat absorbing filter.

and FIG. 5c illustrates the typical transient current characteristics of these two resistive load circuits.

DESCRIPTION OF THE PREFERRED EMBODIMENT

In its preferred embodiment, the illuminating lamp of the invention is comprised of an aluminum reflector 21 in the form of a portion of an ellipsoid of revolution. The light source 17, a high intensity halogen bulb, is mounted horizontally (as shown in FIG. 1A) on a pair of leaf-spring type porcelain sockets 18 with its filament positioned at the near end focus of the ellipsoidal reflector. The electrical power is connected to a power transformer (not shown) in the support arm (not shown), then runs through the swing arm (not shown), the outlets 23 of the fork arm (not shown), alone both side of the lamp housing 1 in a pair of heavy gauge electrical wires 19 to the stem of the porcelain leaf spring socket 18. The reflector 21 is attached by three points to the rediation reflecting disc 16 and the iris control plate 14 with the help of three small thermal insulation porcelain spacers 24. A perforated conic frustem-shaped reflector cover 2 provided for the safety purposes is mounted at the four corners of the lamp body frame 20 together with the light iris control plate 14.

The basic components of the optical zoom mechanism are a fixed lens 5, a moving lens 12, a linear motion platform 7, a pair of linear movement brass guide bars 8, a linear gear rack 10, a spur gear 9, and a linear movement-controlling knob 22. The moving lens 12 is mounted on the perforated aluminum block 13 while a heat absorbing filter 11 is mounted along the same optical axis as the light source and lens 5 on the other side. The body of this perforated aluminum block 13 which is exactly parallel to the iris diaphragm plate 14 is rigidly fastened on the extreme left longitudinal end of the moving platform 7. The two transverse sides of the moving platform 7 are situated in a pair of brass guide bars 8 in a snug fit manner. A linear gear rack 10 mounted on the underside of the moving platform 7 in the longitudinal direction is perfectly matched with a fixed position spur gear 9 in order to form a rack and pinion combination. Because of this, the lens 12 attached to the moving platform 7 will be able to move forward and backward as one desires by turning the control knob 22 in a clockwise or counter-clockwise direction.

The fixed lens 5, which is mounted on the one side of an aluminum lens holder 6 with the dual function color correction front covering glass 4 mounted on the other side, is fastened to the lamp body frame 20. The entire zoom optical assembly is situated inside the housing enclosure 1 with a front covering plate 3 fastened on the front end.

The physical characteristics of the zoom optical assembly are illustrated by FIGS. 2 and 3. As the platform moves toward the light source, the biconvex lens 12 moves toward position A of FIG. 2. The emanating light beam of the halogen bulb 17 will converge at the iris 15 (i.e. the outer focus of the ellipsoidal reflector 21) in a tight bundle along the optical axis forward to the biconvex lens 5. Due to the distance between the lenses and the light bundle tightly centered around the optical axis, the light bundle will converge at a greater distance away from lens 5 before becoming reshaped into a uniformly focused illuminated rectangular area 3 × 4½ inches at a distance of about 32 inches. If lens 12 moves toward position B of FIG. 3, the area of light interception upon lens 12 will be generally increased, the light bundle will spread away from the optical axis, and the distance between the two lens decreases. Consequently, the light beam is bent more severely while passing through lens 5, moving the focused illuminated area close to lens 5. At the extreme position B, the light bundle projects upon the entire surface of lens 12, the light bundle spreads very far away from the optical axis, and there is very short distance between the two lenses, causing the emanating light bundle to be bent more drastically by lens 5. As a result, the light bundle will converge closer to lens 5 and produce a sharply focused rectangular area 1½ × 2 inches at a distance about 13 inches. Since this illuminated area is much smaller and also much closer to lens 5, the brightness of the illuminated area is increased due to (1) increased illumination (i.e. the areal density of the luminous flux on a surface); and (2) the inverse square law of the distance.

Figure 4:
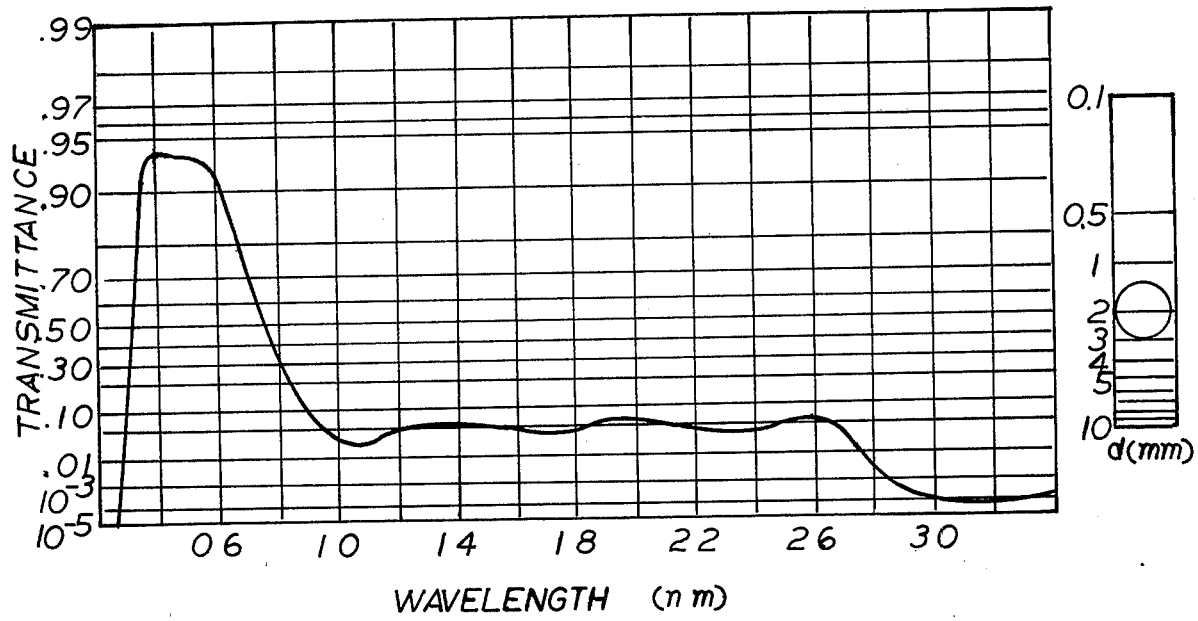

If the capacity of the light source increases beyond 120 watts, there is no heat aborbing filter which will be able to sustain its own high thermal stress without forced ventilation if placed within a distance of 2½ inches from the light source. With lamp of 150 watts or more, the location and physical characteristics of the heat absorbing filter are rather critical. Hence the production of the cold beam illumination upon the appropriate area of a patient is quite complex. For a general purpose dental or medical clinic operating lamp with a light source capacity greater than 150 watts, the heat absorbing filter must be specifically tempered and placed no closer than 3½ inches away from the light source 17. For this invention, a 3 mm (in thickness) by 60 mm (in diameter) tempered KG-1 optical glass with its spectral transmission characteristics as shown in FIGS. 4 and 4a was selected. The figures show the characteristics of peak transmission in the blue region and drops steadily in the green and yellow regions providing a built-in compensation for the drawbacks of incandescent bulb radiation which is inherently rich in green and yellow colors, as well as suppressing the infrared radiation.

The electrical supply circuit of the typical dental operating lamp may be simplified as shown in FIG. 5a. The instantaneous current response throughout the circuit during the instant of switch-on is illustrated by curve (a) of FIG. 5c. The sudden surge of current which can be as much as 120 times the magnitude of the steady-state current will not only induce the phenomena of electrical arcing and deterioration of the switch, but it can eventually lead to a fire hazard throughout the entire electrical power supply system. In addition, this tremendous surge of electrical current will place a great strain which is generally known as the "cold-shock" effect on the tungsten filament of the incandescent halogen bulb 17. Usually this repeated "cold-shock" effect will significantly shorten the service life of the incandescent bulb. These above-mentioned drawbacks can be minimized by using the circuit as shown in FIG. 5b. The ballast resistor $R_P$ functions to produce (1) bypass low power pre-heating of the filament, and (2) shunting during switching. The addition of $R_D$ suppresses switch arcing and controls the current into the filament of the incandescent bulb. The instantaneous electrical current response of this modified load circuit can be illustrated as shown by curve (b) of FIG. 5c. It is very obvious the magnitude of current surge during the instant of switch-on has been reduce to more favorable level.

What I claim is:

1. A zoom operating lamp useful for illuminating the oral cavity during dental and medical surgery, said lamp combination comprising:
   a lamp providing a light source having a uniform beam of light;
   an ellipsoidal reflector having an inner focus and an outer focus, wherein said lamp is positioned at said inner focus thereof;
   an iris positioned at the outer focus of said ellipsoidal reflector;
   a movable biconvex lens; and
   a fixed biconvex lens, said lenses being positioned on the side of said iris opposite said lamp and said reflector which together form a zoom-lens system.

2. A zoom operating lamp as recited in claim 1, wherein there is included a heat-absorbing filter positioned adjacent said movable lens so as to move therewith.

3. A zoom operating lamp as recited in claim 2, wherein there is included a second heat-absorbing filter positioned adjacent said fixed lens.

4. A zoom operating lamp as recited in claim 3, including means for movably mounting said movable lens and its associated heat-absorbing filter.

* * * * *